United States Patent
Chuter et al.

(10) Patent No.: US 7,794,451 B1
(45) Date of Patent: Sep. 14, 2010

(54) IMPLANTABLE CENTRAL VENOUS INJECTION PORT AND EXTERNAL NEEDLE GUIDE

(76) Inventors: Timothy A. M. Chuter, 70 Valley Ct., Atherton, CA (US) 94027; John Maa, 70 Valley Ct., Atherton, CA (US) 94027

( * ) Notice: Subject to any disclaimer, the term of this patent is extended or adjusted under 35 U.S.C. 154(b) by 52 days.

(21) Appl. No.: 12/321,522

(22) Filed: Jan. 22, 2009

Related U.S. Application Data

(63) Continuation of application No. 11/072,778, filed on Mar. 3, 2005, now abandoned.

(60) Provisional application No. 60/550,565, filed on Mar. 5, 2004.

(51) Int. Cl.
    *A61K 9/22* (2006.01)
(52) U.S. Cl. .............. 604/891.1; 604/890.1; 604/892.2; 604/93.01; 604/288.01; 600/30
(58) Field of Classification Search .............. 604/890.1, 604/891.1, 175, 178, 179, 93.01, 535, 536, 604/288.01, 288.02, 288.04, 523; 600/30
    See application file for complete search history.

(56) References Cited

U.S. PATENT DOCUMENTS

| | | | |
|---|---|---|---|
| 4,464,178 A * | 8/1984 | Dalton | 604/174 |
| 6,585,763 B1 * | 7/2003 | Keilman et al. | 623/1.42 |
| 6,652,540 B1 * | 11/2003 | Cole et al. | 606/153 |
| 6,736,797 B1 * | 5/2004 | Larsen et al. | 604/167.05 |
| 7,309,326 B2 * | 12/2007 | Fangrow, Jr. | 604/167.02 |
| 2004/0256584 A1 * | 12/2004 | Zimmerling et al. | 251/7 |

* cited by examiner

*Primary Examiner*—Nicholas D Lucchesi
*Assistant Examiner*—Quynh-Nhu H Vu
(74) *Attorney, Agent, or Firm*—Rader Fishman Grauer

(57) ABSTRACT

An assembly for subcutaneous injections comprising an implantable injection port comprising a body with a plenum, an elastomeric self-sealing diaphragm sealed to the body or with a plenum, an outlet connecting the plenum to a conduit, and one or more ferromagnetic compatible elements positioned about the elastomeric self-sealing diaphragm and near the top side; and a needle support platform comprising a body having a top side and bottom side, with a needle guide extending from the top side to the bottom side, a needle secure; and an attachment base with a top side and bottom side, a center hollow open to the top and bottom sides, and one or more ferromagnetic compatible elements positioned about the center hollow and near the bottom side of the attachment base, the bottom side of the body of the needle support platform resting on the top side of the attachment base and slidable thereon, the position of the body on the attachment base adapted to be detachably secured.

13 Claims, 3 Drawing Sheets

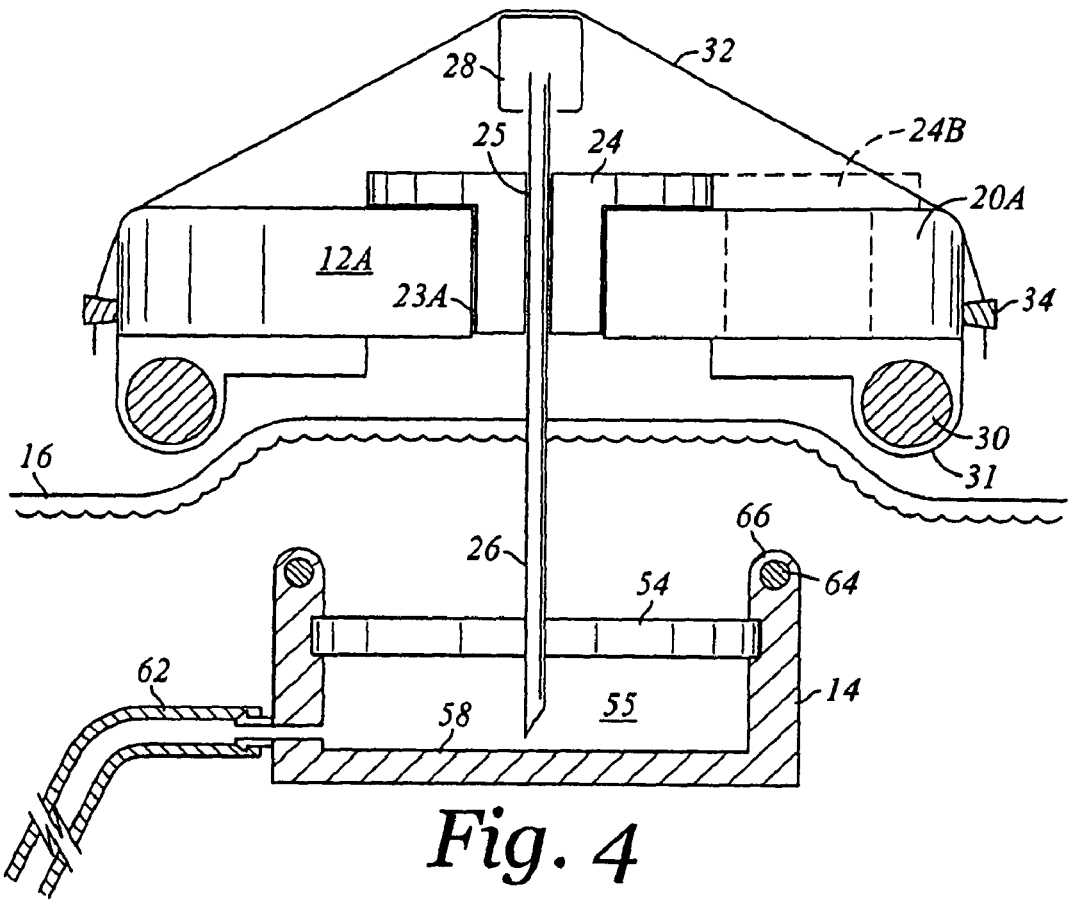
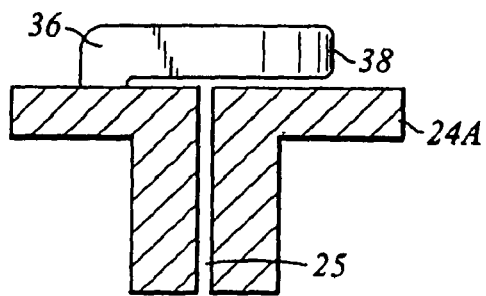
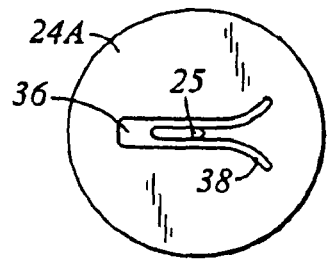

IMPLANTABLE CENTRAL VENOUS INJECTION PORT AND EXTERNAL NEEDLE GUIDE

This application is continuation of U.S. patent application Ser. No. 11/072,778, filed on Mar. 3, 2005 now abandoned, and claims the benefit of U.S. Provisional Application No. 60/550,565, filed on Mar. 5, 2004.

FIELD OF THE INVENTION

The present invention is directed to an implantable injection port for a central venous catheter and to an assembly including the implantable injection port and an external needle guide and support.

BACKGROUND OF THE INVENTION

Implantable central venous catheters have been in use for several years and have many advantages for long-term venous access, particularly in cancer patients requiring chemotherapy and/or continuous doses of painkillers. The central location of the catheter tip in a high flow volume vein, such as a return vein to the heart, allows chemotherapeutic agents, which are toxic, to be quickly diluted by the high blood flow through the vein, minimizing local tissue damage and inflammation from the injected medicinal agent. However, needle puncture of the injection port is not necessarily easy or secure. In obese patients, the location or position of a port implanted close to the skin surface is frequently unstable because the implant is within the subcutaneous fat. If the injection port is placed in a more stable location in an obese patient, such as on the pectoral fascia, the port is then positioned far from the skin surface, making a successful injection of the port more difficult. In either situation, there is a risk of accidental subcutaneous infiltration of the agents because of the needle missing the injection port. Subcutaneous infiltration of chemotherapeutics, which are very toxic, can cause severe inflammation and necrosis of tissue. This can lead to severe complications and is especially detrimental to patients that are already debilitated and/or in fragile condition. Even when the needle tip position has been established by blood withdrawal prior to penetration of the injection port, there is no guarantee that the needle will stay in position within the port for the duration of the infusion of a chemotherapy agent and/or other medicinal agent.

It is an object of the present invention to provide a needle guide and support platform that can be readily positioned directly over the implanted injection port.

It is a further object of the present invention to provide a needle guide and support platform and implanted injection port that are mutually attracted to one another.

An even further object of the present invention is to provide an assembly that ensures the proper needle position and orientation with respect to the injection port through the mutual attraction by electro or permanent magnets or ferromagnetic bodies in the needle guide and support platform and ferromagnetic materials or permanent magnets in the implantable injection port to bring the assembly as close together as possible and to position and orient the needle with respect to the injection port, and to maintain the assembly in position during infusion.

SUMMARY OF THE INVENTION

In one embodiment of the present invention, the invention is directed to an assembly for subcutaneous injections comprising an implantable injection port comprising a body with a plenum, and a top side and bottom side; an elastomeric self-sealing diaphragm sealed to the body over the plenum, the body having an outlet port connecting the plenum to a central venous catheter, and one or more ferromagnetic compatible elements positioned about the elastomeric self-sealing diaphragm and near the top side of the body; and a needle support platform comprising a body having a top side and a bottom side, a needle guide extending from the top side to the bottom side, a needle securer, and one or more ferromagnetic compatible elements positioned about the needle guide and near the bottom side, the ferromagnetic compatible elements of the implantable injection port having opposite polarities to the ferromagnetic compatible elements of the needle support platform.

The needle support platform can have two or more pins on its body to engage a line adapted to engage and to secure the needle in the needle support.

Preferably the ferromagnetic compatible element of the implantable injection port is a ring-shaped element of a first diameter.

The ferromagnetic compatible element of the implantable injection port is preferably a permanent magnet ring of a first diameter.

The ferromagnetic compatible element of the needle support platform is a ring-shaped element with a diameter at least equal to the first diameter. Preferably the inner diameter of the ferromagnetic compatible ring-shaped element of the needle support platform has a diameter greater than the outer diameter of the ferromagnetic compatible ring-shaped element of the implantable injection port.

Preferably the ferromagnetic compatible element of the needle support is a permanent magnet ring having a diameter at least equal to the first diameter. More preferably the inner diameter of the permanent magnet ring of the needle support platform has an inner diameter greater than the outer diameter of the ferromagnetic compatible ring-shaped element of the implantable injection port.

In the preferred embodiment, the body of the implantable injection port has a ring-shaped lip extending outward from the front side and one or more ferromagnetic compatible elements positioned at least partially in the ring-shaped lip.

Preferably the body of the needle support platform has a ring-shaped lip extending downward from its bottom side and the one or more ferromagnetic compatible elements are positioned at least partially in the ring-shaped lip.

Preferably the ferromagnetic compatible elements of the body of the needle support platform have a ring lip extending downward from the bottom side and the one or more ferromagnetic compatible elements are positioned at least partially in the ring lip.

Preferably the outer diameter of the ring-shaped lip of the implantable injection port is less than the inner diameter of the ring-shaped lip of the needle support platform.

In a further embodiment of the present invention, the invention is directed to an assembly for subcutaneous injections comprising an implantable injection port comprising a body with an enclosed plenum, an elastomeric self-sealing diaphragm sealed to the body and forming a all of the plenum, an outlet connecting the plenum to a central venous catheter, and one or more ferromagnetic compatible elements positioned about the elastomeric self-sealing diaphragm and near the top side; and a needle support platform comprising a body having a top side, bottom side, and a perimeter side wall with a needle guide extending from the top side to the bottom side, a needle securer; and an attachment base with a top side and bottom side, a center hollow open to the top and bottom sides, and one or more ferromagnetic compatible elements positioned about the center hollow and near the bottom side of the attachment base, the bottom side of the body of the needle support moveably secured to on the top side of the attachment base with the body and a lock to lock the attachment base to the body.

Preferably the ring-shaped lip of the injection port can nestle in the ring-shaped element of the needle guide and support with the skin in between to align the port and needle guide for the needle injection and infusion.

BRIEF DESCRIPTION OF THE DRAWINGS

FIG. 4 is a side cross-sectional view of another embodiment of the assembly for subcutaneous injections of the present invention;

FIG. 5 is a side plan view of another embodiment of the needle guide of the present invention; and FIG. 6 is a top plan view of the needle guide of FIG. 5.

DETAILED DESCRIPTION OF THE INVENTION

Figure 1:
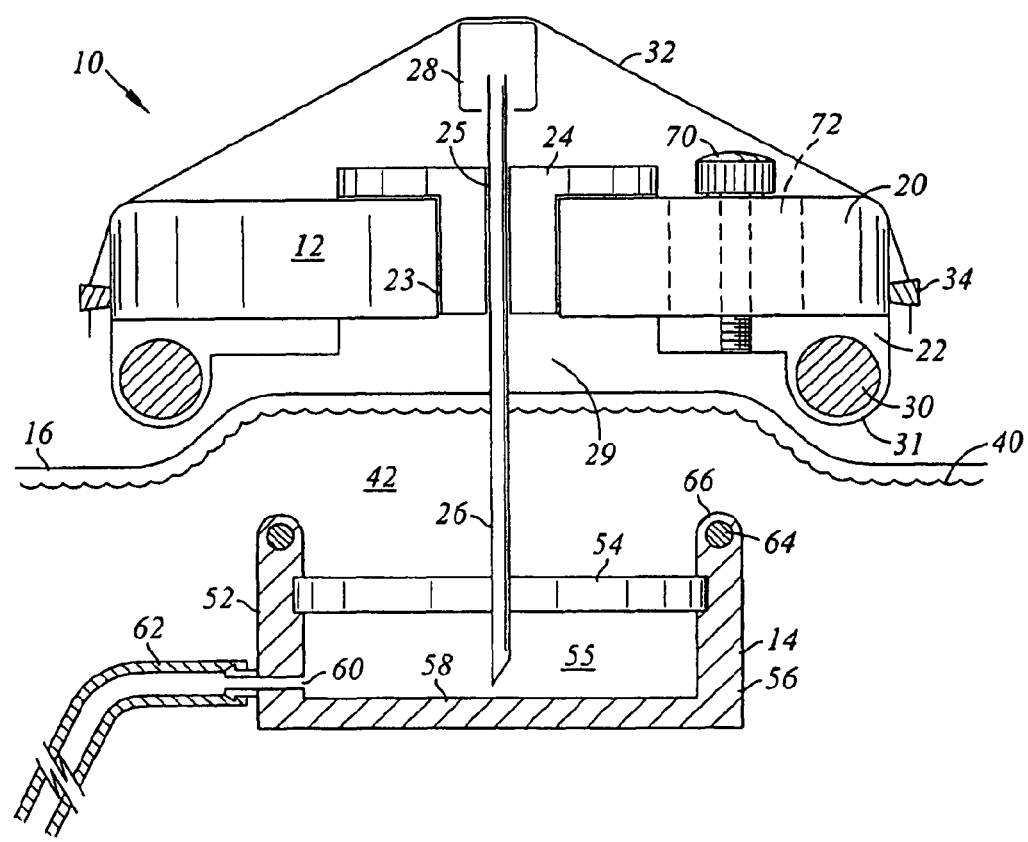
FIG. 1 is a side cross-sectional view of the assembly for subcutaneous injections of the present invention.
Figure 2:
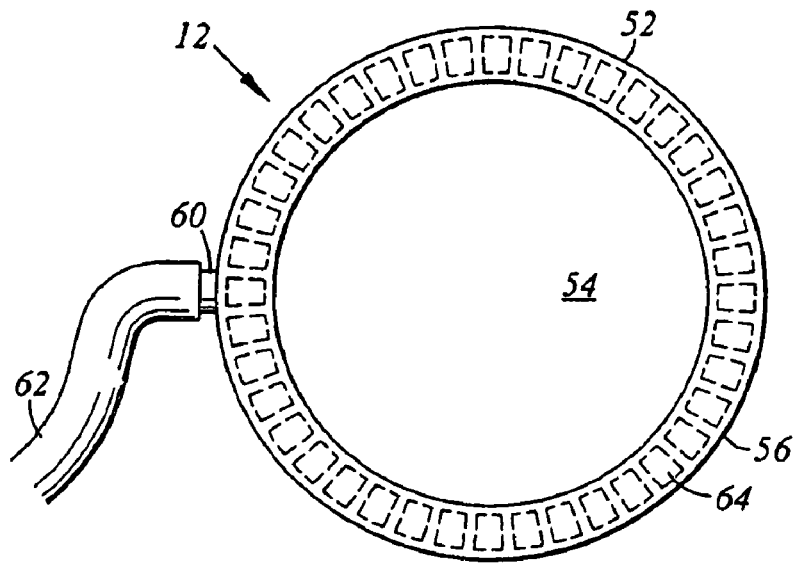
FIG. 2 is a top plan view of the implantable injection port of the present invention.
Figure 3:
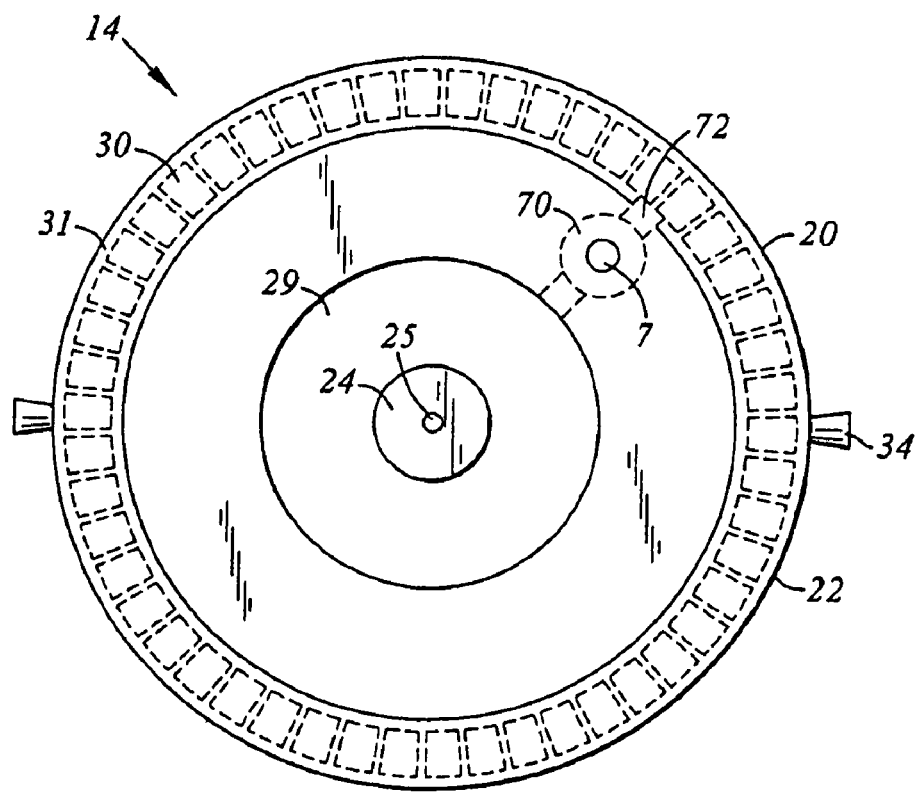
FIG. 3 is a bottom plan view of the needle support platform of the present invention.

Referring to FIGS. 1-3, the needle guide and port assembly 10 of the present invention is shown in use on a patient. The invention comprises an external needle guide and support 12 which is used on the exterior surface of a patient and a subcutaneous injection port 14 which is implanted into the patient and connected to a central venous catheter 62. FIG. 1 is not to scale and shows the assembly in an enlarged view. The external needle guide and support platform 12 comprises a body 20 and an attachment base 22. The body has a central bore 23 in which is inserted a sterile needle guide 24. The needle guide 24 has a central bore 25 which extends the length of it and is adapted to receive a hypodermic needle 26. Preferably the needle bore 25 receives the hypodermic needle 26 in a close relationship similar to a friction fit to properly align the needle and to prevent the needle from freely moving up or down within the needle bore. The hypodermic needle has a connector 28 at one end which is adapted to fit on a hypodermic syringe or to other attachment assemblies for feeding fluids into the needle. To prevent the needle from being forced out of the implantable injection port during infusion, the needle can be secured in the needle guide and support platform by a line 32 which is connected to the pins 34 on the body either by wrapping a line around the pins or by having loops at the end of the line which engage the pins.

In an alternative embodiment of the present invention (FIGS. 5 and 6), the needle guide 24A can have a retaining clip 36 which has two fingers 38 which are pinched bias to come together. The needle shank of the hypodermic needle 26 passes through the fingers 38 into the needle bore 25. The fingers pinch the shank of the needle and prevent the hypodermic needle from moving up or down. The fingers can be expanded outwardly to permit the needle to be pushed downward, or repositioned, or withdrawn. Other methods can also be employed to maintain the hypodermic needle in a fixed position with respect to the needle guide and support platform following insertion of the needle tip through the septum 54 into the plenum 55 of the implanted injection port.

The bottom surface of the body 20 is moveably secured on the top surface of the attachment base 22. The attachment base has a hollow 29 in the center thereof through which the needle 26 can pass. On the outer perimeter of the attachment base, a permanent magnet ring 30 is secured within the attachment base in ring-shaped lip or protrusion 31. The needle guide and support platform and implantable injection port are illustrated with permanent magnet rings 30 and 64. The permanent magnets have opposite polarity to attract them to one another. However, ferromagnetic compatible elements may be employed including an electromagnetic, a ferromagnetic material such as iron, and the like. If a ferromagnetic material, such as iron is employed in the needle guide and support platform, then the implantable injection port will have a permanent magnet as described below, and vice versa. An electromagnet can be used in the needle guide and support platform. A continuous ring magnet is illustrated in the drawings; however, the magnet does not necessarily have to be a closed ring or ring-shape. Moreover, the ferromagnetic compatible material can be made up of separate magnetic bars or ferromagnetic materials or separate electromagnets. The needle guide and support platform does not have a size limitation as the implantable injection port has. Thus, the compatible ferromagnetic material on the needle guide and support platform 12 will preferably be a permanent magnet or electromagnet. Preferably both ports 12 and 14 of the assembly 10 have permanent magnets of opposite polarity.

To keep the position of the body and the attachment base of the needle guide and support fixed for insertion of the needle into the implantable injection port and for infusion, the body 20 has a longitudinal slot 72 extending from the top side to the bottom side through which passes a holding screw 70. The shank of the holding screw passes through the slot 72 and engages a threaded bore 74 in the attachment base. The threaded screw is loosened to adjust the position of the body on the attachment base. The thread screw is tightened down to fix the position of the body to the attachment base. The body can be repositioned with respect to the attachment base and with respect to the septum 54 of the implanted injection port 14 for each infusion to prevent multiple needle insertions on one location of the septum. The needle guide 24 is replaceable and preferably is supplied in sterile packaging.

Prior to using the assembly of the present invention, the implantable injection port 14 is surgically implanted into a patient, normally in the torso, and the implantable injection port is connected to a central venous catheter 62 which has its far end (not shown) inserted into a large vein with a rapid blood flow to provide quick dilution of the material being infused into the patient. The therapeutic agent is fed into the needle and flows into the plenum 54 and out the outlet port 60 into the central venous catheter 62.

The implantable injection port has a body 52 and a elastomeric self-sealing septum or diaphragm 54 which is sealed to the body and forms a wall of the enclosed plenum 55 within the implantable injection port. The plenum is connected to outlet port 60 through which the material being infused into the patient passes, and then passes into the central venous catheter 62. The body has perimeter side walls 56 which are connected to the base wall 58. The top of the perimeter side walls forms a ring-shaped lip 66 in which a permanent magnet ring 64 or other ferromagnetic compatible material as discussed above is embedded.

The nurse or technician that is to carry out infusion locates the implanted implantable injection port 14 within the body of the patient. The port is normally situated relatively close to the skin and can be easily felt. A position of the body 20 to the attachment base 22 is fixed by loosening and tightening the thread screw to set the position of the body to the attachment base. The needle guide and support platform are positioned over the location of the implanted port. Because of the shape of the ring-shaped lip or protrusion extending from the bottom side of the attachment base and the ring-shaped lip or protrusion created by the top of the perimeter wall of the injection port, the influence of the magnetic attraction between the ferromagnetic compatible materials of the platform and injection port draw the platform and injection port together in alignment which positions the needle guide with the septum of the injection port. When the outer diameter of the ring-shaped lip of the implantable injection port fits within the ring-shaped lip of the needle guide and support platform, this aids in aligning the needle guide and support platform with the implantable injection port.

Referring to FIG. 4, an alternative embodiment of the present invention is illustrated. Most of the components of the assembly of FIG. 4 are identical to the components of the assembly of FIG. 1 and the identical components are identified by the same numbers and will not be described again. The difference in the embodiment between FIG. 1 and FIG. 4 is the needle guide and support platform 20A. The platform 20A does not have a separate body 20 and support platform 22, but rather is a unitary element. The platform 23A has a bore which receives a needle guide 24. The needle guide has a needle bore 25 which is adapted to receive a hypodermic needle 26. The needle guide and support platform 12A are utilized in the same manner as the needle guide and support platform 12 of FIG. 1. The needle guide and support platform of 12A does not have the ability to independently move the needle guide and needle with respect to the implantable injection port 14. When this needle guide and support platform 12A are utilized, the septum 54 of the implantable injection port is penetrated in approximately the same location each time the needle is inserted through the septum 54 into the plenum 55 for the feeding or infusion of a therapeutic agent. In an alternative embodiment, the needle guide 24B is not positioned in the center of the body, but rather off to one side (shown in phantom). This provides that the needle will not necessarily penetrate the same area of the septum since the needle guide 12 and port 14 are not circumferentially aligned for each use, i.e. the needle guide will usually be rotationally positioned differently during each use with respect to the injection port because the needle guide and injection port are not rotationally aligned.

Although the present invention has been described with respect to specific embodiments, the invention is not limited to the specific embodiments disclosed, but is intended to cover assemblies with equivalent components that position, orient and support the hypodermic needle for injection into a implantable injection port and to draw the needle guide and support platform and the implantable injection port together.

What is claimed is:
1. An assembly for subcutaneous injections comprising:
an implantable injection port having a body with a plenum;
an elastomeric self-sealing diaphragm sealed to the body over the plenum;
an outlet for connecting the plenum to a central venous catheter;
one or more ferromagnetic compatible elements positioned about the elastomeric self-sealing diaphragm and near the top side of the body of said injection port;
an external needle guide and support platform comprising a body having a top side; bottom side; and an attachment base; wherein said attachment base directly connected to said body of said needle guide;
a needle guide extending from the top side to the bottom side;
a needle securer; and
one or more ferromagnetic compatible elements positioned near the bottom side and within a ring-shaped lip of the attachment base, the ferromagnetic compatible elements of the implantable injection port having opposite polarities to the ferromagnetic compatible elements of the needle support platform.

2. The assembly according to claim 1 wherein the needle support has two or more pins on its body, and the needle securer comprises a line adapted to engage the pins to secure the needle in the needle support.

3. The assembly according to claim 1 wherein the ferromagnetic compatible element of the implantable injection port is a ring of a first diameter.

4. The assembly according to claim 1 wherein the ferromagnetic compatible element of the implantable injection port is a permanent magnet ring of a first diameter.

5. The assembly according to claim 1 wherein the ferromagnetic compatible element of the needle support platform is a ring with a diameter at least equal to the first diameter.

6. The assembly according to claim 5 wherein the diameter of the ferromagnetic compatible element ring of the needle support platform has a diameter greater than the first diameter.

7. The assembly according to claim 1 wherein the ferromagnetic compatible element of the needle support is a permanent magnet ring having a diameter at 15 least equal to the first diameter.

8. The assembly according to claim 7 wherein the diameter of the permanent magnet ring of the needle support platform and the diameter greater than the first diameter.

9. The assembly according to claim 1 wherein the body of the implantable injection port has a ring lip extending outward from the front side and one or more ferromagnetic compatible elements positioned at least partially in the ring lip.

10. The assembly according to claim 1 wherein the body of the needle support platform has a ring lip extending downward from the bottom side and the one or more ferromagnetic compatible elements are positioned at least partially in the ring lip.

11. The assembly according to claim 9 wherein the body of the needle support platform has a ring lip extending downward from the bottom side and the one or more ferromagnetic compatible elements are positioned at least partially in the ring lip.

12. The assembly according to claim 11 wherein the outer diameter of the ring lip of the implantable injection port is less than the inner diameter of the ring lip of the needle support platform.

13. An assembly for subcutaneous injections comprising:
an implantable injection port comprising: a body with a plenum, an elastomeric self-sealing diaphragm sealed to the body or with a plenum, an outlet connecting the plenum to a conduit, and one or more ferromagnetic compatible elements positioned about the elastomeric self-sealing diaphragm and near the top side; and
an external needle guide and support platform comprising: a body having a top side and bottom side, with a needle guide extending from the top side to the bottom side, a needle secure; and an attachment base with a top side and bottom side, a center hollow open to the top and bottom sides, and one or more ferromagnetic compatible elements positioned within a ring-shaped lip of the attachment base and near center hollow, the bottom side of the body of the external needle guide and support platform resting on the top side of the attachment base and slidable thereon, the position of the body on the attachment base adapted to be detachably secured.

* * * * *